US012646628B2

(12) United States Patent
Shah et al.

(10) Patent No.: US 12,646,628 B2
(45) Date of Patent: Jun. 2, 2026

(54) MACHINE LEARNING MODELS FOR AUTOMATED SELECTION OF EXECUTABLE SEQUENCES

(71) Applicant: Evernorth Strategic Development, Inc., St. Louis, MO (US)

(72) Inventors: Mayank K. Shah, Kildeer, IL (US); Chelsea Drake, Virginia Beach, VA (US); Robert Monzyk, St. Louis, MO (US); Alexi E. Makarkin, Ballwin, MO (US); Biswajit Maity, Kolkata (IN); Andrew Telle, Birmingham, AL (US); Christopher G. Lehmuth, St. Louis, MO (US); Brandon Phan, St. Louis, MO (US)

(73) Assignee: Evernorth Strategic Development, Inc., St. Louis, MO (US)

( * ) Notice: Subject to any disclaimer, the term of this patent is extended or adjusted under 35 U.S.C. 154(b) by 1233 days.

(21) Appl. No.: 17/347,849

(22) Filed: Jun. 15, 2021

(65) Prior Publication Data

US 2022/0399132 A1 Dec. 15, 2022

(51) Int. Cl.
*G16H 80/00* (2018.01)
*G06F 18/214* (2023.01)
(Continued)

(52) U.S. Cl.
CPC .......... *G16H 80/00* (2018.01); *G06F 18/214* (2023.01); *G06N 3/082* (2013.01); *G06N 20/20* (2019.01); *G16H 50/20* (2018.01); *G16H 50/70* (2018.01)

(58) Field of Classification Search
CPC ........ G06H 80/00; G16H 50/70; G16H 50/20; G06N 20/20; G06N 3/082; G06F 18/214
See application file for complete search history.

(56) References Cited

U.S. PATENT DOCUMENTS 8,671,040 B2 3/2014 Roser
9,349,105 B2 5/2016 Beymer
(Continued)

FOREIGN PATENT DOCUMENTS

AU 2021101323 A4 5/2021

OTHER PUBLICATIONS

Homer, et al., Predicting Falls in People Aged 65 Years and Older from Insurance Claims. Am J Med. Jun. 2017; 130(6):744.e17-744. e23. doi: 10.1016/j.amjmed.2017.01.003. Epub Jan. 20, 2017. PMID: 28111165; PMCID: PMC5441951.
(Continued)

*Primary Examiner* — Sherrod L Keaton
(74) *Attorney, Agent, or Firm* — Miller Johnson

(57) ABSTRACT

A computer system includes processor hardware configured to execute instructions from memory hardware. The instructions include training a machine learning model to generate an entity expiration likelihood output, obtaining a set of multiple database entities, and processing, by the machine learning model, feature vector inputs associated with each database entry to generate an entity expiration likelihood output. The instructions include determining a subset of the database entities having the highest entity expiration likelihood outputs, and, for each database entity in the subset, determining output impact scores for parameters of the feature vector input associated with the database entity, generating a feature list based on the determined output impact scores, and automatically selecting an executable sequence according to the entity expiration likelihood output associated with the database entity. The feature list is specific to the database entity and includes one or more of the parameters having the highest output impact scores.

20 Claims, 7 Drawing Sheets

(51) Int. Cl.

| | | |
|---|---|---|
| *G06N 3/082* | (2023.01) | |
| *G06N 20/20* | (2019.01) | |
| *G16H 50/20* | (2018.01) | |
| *G16H 50/70* | (2018.01) | |

(56) References Cited

U.S. PATENT DOCUMENTS

| | | | |
|---|---|---|---|
| 9,667,641 | B2 | 5/2017 | Muddu |
| 9,886,288 | B2 | 2/2018 | Baird |
| 10,102,482 | B2 | 10/2018 | Cheng |
| 10,257,660 | B2 | 4/2019 | Price |
| 10,438,133 | B2 | 10/2019 | Vachhani |
| 10,516,906 | B2 | 12/2019 | Arpteg |
| 10,628,431 | B2 | 4/2020 | Chittar |
| 10,628,432 | B2 | 4/2020 | Guo |
| 10,630,706 | B2 | 4/2020 | Devi Reddy |
| 10,977,728 | B1 | 4/2021 | Sanderson |
| 2011/0071363 | A1* | 3/2011 | Montijo ................. G06Q 10/10 600/300 |
| 2012/0066163 | A1* | 3/2012 | Balls ........................ G06N 3/08 435/6.12 |

| | | | |
|---|---|---|---|
| 2014/0257832 | A1 | 9/2014 | Hermiz |
| 2016/0203221 | A1 | 7/2016 | Rao |
| 2017/0071549 | A1* | 3/2017 | Seely .................. A61B 5/7275 |
| 2017/0213145 | A1 | 7/2017 | Pathak |
| 2018/0181704 | A1* | 6/2018 | Stupp ..................... G16B 20/00 |
| 2020/0005214 | A1 | 1/2020 | Kulkarni |
| 2020/0118689 | A1 | 4/2020 | Luthy |
| 2020/0134430 | A1* | 4/2020 | Yamashita ........... G06N 3/0499 |
| 2020/0356878 | A1 | 11/2020 | Lakshmipathy |
| 2020/0356900 | A1 | 11/2020 | Briancon |
| 2020/0387833 | A1 | 12/2020 | Kursun |
| 2022/0115098 | A1 | 4/2022 | Speirs |
| 2022/0375617 | A1 | 11/2022 | Ji |

OTHER PUBLICATIONS

MedlinePlus, Fall Risk Assessment, https://medlineplus.gov/lab-tests/fall-risk-assessment/, Sep. 13, 2021.

Roshdibenam et al, Machine Learning Prediction of Fall Risk in Older Adults Using Timed Up and Go Test Kinematics. Sensors (Basel). May 17, 2021;21(10):3481. doi: 10.3390/s21103481. PMID: 34067644; PMCID: PMC8156094.

\* cited by examiner

Example feature list for a high-risk patient

Patient ID:　　XXXX

Prediction score:　0.8

| FACTOR # | INPUT FEATURE | VALUE | DESCRIPTION |
|---|---|---|---|
| Factor 1 | Age | 89 | Age of the patient |
| Factor 2 | ICD: Encounter for palliative care | 25 | Specific ICD description |
| Factor 3 | ICD: Dementia | 1 | Patient suffering from dementia |
| Factor 4 | Gender | M | Gender of the patient |
| Factor 5 | CPT: 99308 Subsequent Nursing facility care | 25 | Current procedure codes applied to a patient |
| Factor 6 | CPT: A0428 _ BLS | 1 | Ambulance service, basic life support, non-emergency transport |
| Factor 7 | Customer cost of claim | 8825 | Customer cost of medical claims |
| Factor 8 | Medicine: Furosemide | 1 | Medicine consumed by a patient |
| Factor 9 | Medicine: Ipratropium Albuterol | 1 | Medicine consumed by a patient |
| Factor 10 | Number of unique CPT codes | 28 | Number of unique CPT codes applied to a patient |

FIG. 7

MACHINE LEARNING MODELS FOR AUTOMATED SELECTION OF EXECUTABLE SEQUENCES

FIELD

The present disclosure relates to machine learning models that generate expiration likelihood estimates for database entries for automatically selecting executable sequences associated with the database entries.

BACKGROUND

As the elderly population lives longer with chronic conditions, the need for end-of-life care management becomes increasingly important in patients' lives. Optimized care management may prevent unnecessary hospitalizations, diagnostic and treatment interventions, and intensive and emergency department care, to reduce waste in healthcare. Historically, palliative care programs are often confused with hospice, may disrupt the continuity of care, and can be expensive compared to alternatives.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A computer system includes memory hardware configured to store a machine learning model, historical feature vector inputs, and computer-executable instructions. The historical feature vector inputs include historical data structures specific to multiple historical database entities. The system includes processor hardware configured to execute the instructions. The instructions include training the machine learning model with the historical feature vector inputs to generate an entity expiration likelihood output. The training includes, for each expired entity of the multiple historical database entities, determining an expiration date of the expired entity, and generating a random offset time value for the expired entity, wherein the historical feature vector input for the expired entity includes only historical data structures that are dated prior to the expiration date of the expired entity minus the random offset time value. The instructions include obtaining a set of multiple database entities, and for each database entity in the set of multiple database entities, obtaining structured input data specific to the database entity, generating a feature vector input according to the structured input data, processing, by the machine learning model, the feature vector input to generate the entity expiration likelihood output, and storing the entity expiration likelihood output in association with the database entity. The instructions include determining a subset of the multiple database entities having the highest entity expiration likelihood outputs, and for each database entity in the subset, determining output impact scores for parameters of the feature vector input associated with the database entity, each output impact score indicative of an effect of the parameter on the entity expiration likelihood output for the database entity, generating a feature list based on the determined output impact scores. The feature list is specific to the database entity and includes one or more of the parameters having the highest output impact scores, and automatically selecting an executable sequence according to the entity expiration likelihood output associated with the database entity.

In other features, training the machine learning model includes generating a random offset time value for each non-expired entity of the multiple historical database entities, the historical feature vector input for each non-expired entity includes only historical data structures that are dated prior to an end date of the historical data structures specific to the non-expired entity minus the random offset time value, and a distribution of the random offset time values for the expired entities is equal to a distribution of the random offset time values for the non-expired entities. In other features, generating the feature list includes, for each of the one or more parameters, removing the parameter from the feature list in response to determining that the parameter is negatively correlated with the entity expiration likelihood output for the database entity.

In other features, the instructions further include generating an archive report including the entity expiration likelihood output and feature list for each database entity in the subset, and storing the archive report in an archive database on a periodic basis. In other features, automatically selecting the executable sequence includes automatically scheduling a palliative care intervention for the database entity. In other features, the palliative care intervention includes at least one of a text message intervention, an email intervention, an automated phone call intervention, and a live phone call intervention.

In other features, automatically selecting the executable sequence includes automatically scheduling the database entity to a palliative care case management database. In other features, training the machine learning model includes comparing multiple entity expiration likelihood outputs of the machine learning model to the historical data structures, determining whether an accuracy of the comparison is greater than or equal to a specified accuracy threshold, adjusting parameters of the machine learning model or selecting a different machine learning model type for retraining the machine learning model, in response to the accuracy of the comparison being less than the specified accuracy threshold, and saving the machine learning model for use in generating entity expiration likelihood outputs, in response to the accuracy of the comparison being greater than or equal to the specified accuracy threshold.

In other features, training the machine learning model includes training multiple machine learning model types simultaneously or in succession, identifying one of the multiple machine learning model types having a highest output accuracy compared to others of the machine learning model types, and saving the identified machine learning model type having the highest output accuracy for use in generating entity expiration likelihood outputs. In other features, training the machine learning model includes separating portions of the historical feature vector inputs into structured training data and structured test data, training the machine learning model using the structured training data, testing the trained machine learning model using the structured test data, evaluating results of testing the trained machine learning model, and saving the machine learning model for use in generating entity expiration likelihood outputs, in response to an accuracy of the evaluated results being greater than or equal to a specified accuracy threshold.

In other features, training the machine learning model includes training a light gradient boosted tree model. In other features, generating the feature vector input includes generating the feature vector input according to at least one of structured claim data specific to the database entity, structured demographic data specific to the database entity, structured lab test data specific to the database entity, structured event data specific to the database entity, structured social depravation index (SDI) score data specific to the database entity, structured pharmacy data specific to the database entity, and structured patient data specific to the database entity. In other features, generating the random offset time value includes randomly selecting a day within a six to twelve month time period prior to the expiration date of the historical database entity, and the historical feature vector input for the expired entity includes only historical data structures that are dated within a twelve month time period prior to the expiration date of the expired entity minus the random offset time value.

A computerized method for automated selection of executable sequences includes training a machine learning model with historical feature vector inputs to generate an entity expiration likelihood output. The historical feature vector inputs include historical data structures specific to multiple historical database entities. The training includes, for each expired entity of the multiple historical database entities, determining an expiration date of the expired entity, and generating a random offset time value for the expired entity, wherein the historical feature vector input for the expired entity includes only historical data structures that are dated prior to the expiration date of the expired entity minus the random offset time value. The method includes obtaining a set of multiple database entities, and for each database entity in the set of multiple database entities, obtaining structured input data specific to the database entity, generating a feature vector input according to the structured input data, processing, by the machine learning model, the feature vector input to generate the entity expiration likelihood output, and storing the entity expiration likelihood output in association with the database entity. The method includes determining a subset of the multiple database entities having the highest entity expiration likelihood outputs, and for each database entity in the subset, determining output impact scores for parameters of the feature vector input associated with the database entity, each output impact score indicative of an effect of the parameter on the entity expiration likelihood output for the database entity, generating a feature list based on the determined output impact scores. The feature list is specific to the database entity and includes one or more of the parameters having the highest output impact scores, and automatically selecting an executable sequence according to the entity expiration likelihood output associated with the database entity.

In other features, training the machine learning model includes generating a random offset time value for each non-expired entity of the multiple historical database entities, the historical feature vector input for each non-expired entity includes only historical data structures that are dated prior to an end date of the historical data structures specific to the non-expired entity minus the random offset time value, and a distribution of the random offset time values for the expired entities is equal to a distribution of the random offset time values for the non-expired entities. In other features, generating the feature list includes, for each of the one or more parameters, removing the parameter from the feature list in response to determining that the parameter is negatively correlated with the entity expiration likelihood output for the database entity.

In other features, the method includes generating an archive report including the entity expiration likelihood output and feature list for each database entity in the subset, and storing the archive report in an archive database on a periodic basis. In other features, automatically selecting the executable sequence includes automatically scheduling a palliative care intervention for the database entity. In other features, the palliative care intervention includes at least one of a text message intervention, an email intervention, an automated phone call intervention, and a live phone call intervention. In other features, automatically selecting the executable sequence includes automatically scheduling the database entity to a palliative care case management database.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

FIG. 7 is a graphical representation of an example feature list generated by the process of FIG. 6.

In the drawings, reference numbers may be reused to identify similar and/or identical elements.

DETAILED DESCRIPTION

Patients with complex health conditions may improve their quality of life and alleviate physical and mental burden in a non-hospice setting by taking advantage of care coordination, polypharmacy, symptom management, advanced care plans, and psychosocial assessments. In various implementations, a machine learning model may be used to facilitate palliative care teams relying on enhanced decision tools for expedient care assessment, thus allowing palliative care program resources to be deployed to patients who may gain the greatest benefits.

Machine learning models may augments and enhances clinical assessments by, for example, using a stratified approach and uncovering the best patient candidates for enrollment to a palliative care program. Goals of using the model may include having patients begin palliative care earlier, improve patients' quality of life, and reducing overall cost to patients and payers. In various implementations, an artificial intelligence machine learning model may identify up to five times the patients or more that score highest on a palliative care suitability scale during the next three to twelve months of the patients' lives, as compared to a non-model approach. For example, some machine learning models may correctly identify 44.2% of candidates (or more or less) by focusing on a top 1% of all plan members scored by the model regardless of underlying health conditions.

Automated Sequence Selection System

Figure 1:
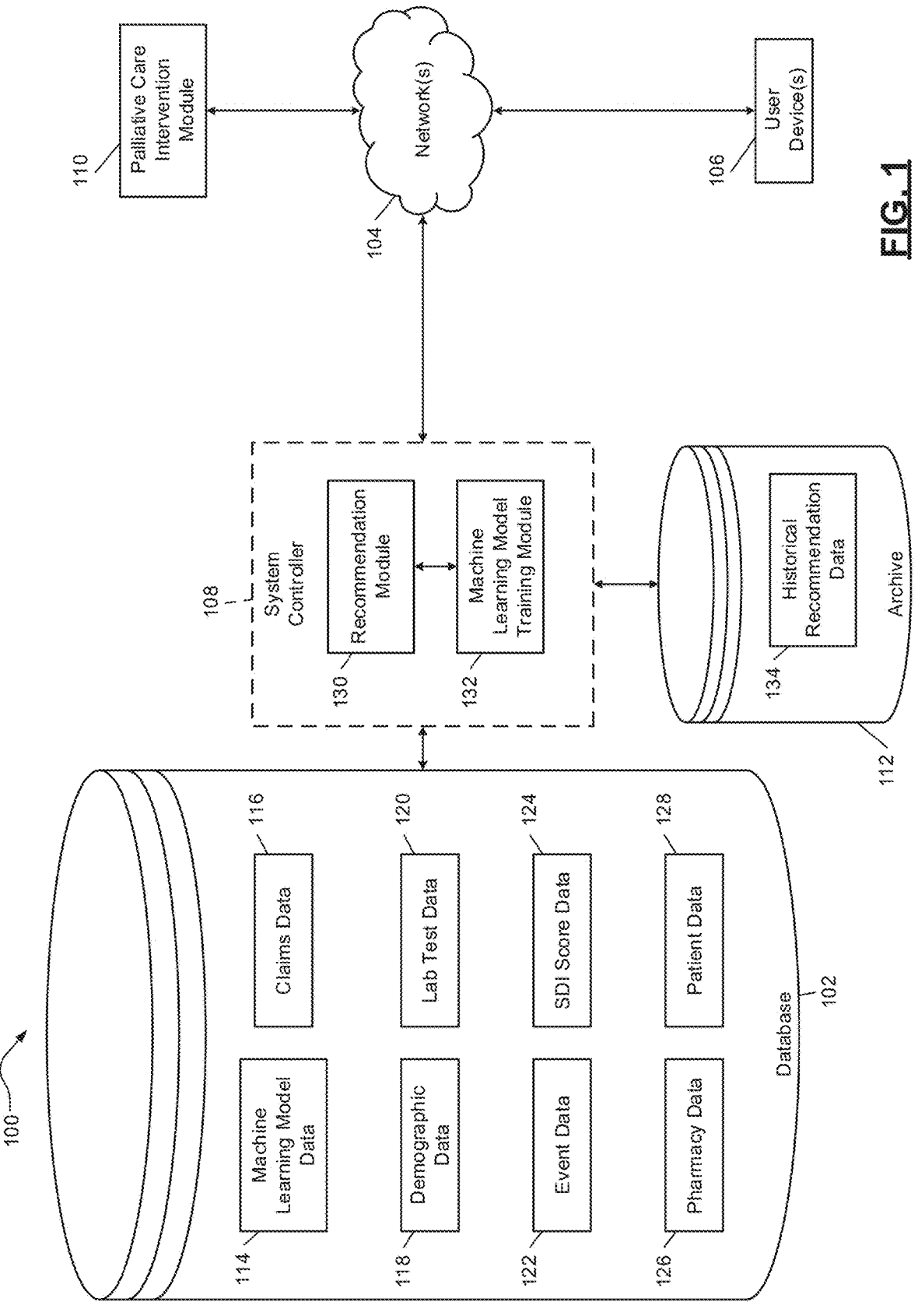
FIG. 1 is a functional block diagram of a system for automated selection of executable sequences.

FIG. 1 is a functional block diagram of an example system 100 for automated selection of executable sequences, which includes a database 102. While the system 100 is generally described as being deployed in a computer network system, the database 102 and/or components of the system 100 may otherwise be deployed (for example, as a standalone computer setup). The system 100 may include a desktop computer, a laptop computer, a tablet, a smartphone, etc.

As shown in FIG. 1, the database 102 stores machine learning model data 114, claims data 116, demographic data 118, lab test data 120, event data 122, social deprivation index (SDI) score data 124, pharmacy data 126, and patient data 128. In various implementations, the database 102 may store other types of data as well. The machine learning model data 114, claims data 116, demographic data 118, lab test data 120, event data 122, SDI score data 124, pharmacy data 126, and patient data 128 may be located in different physical memories within the database 102, such as different random access memory (RAM), read-only memory (ROM), a non-volatile hard disk or flash memory, etc. In some implementations, machine learning model data 114, claims data 116, demographic data 118, lab test data 120, event data 122, SDI score data 124, pharmacy data 126, and patient data 128 may be located in the same memory (such as in different address ranges of the same memory). In various implementations, the machine learning model data 114, claims data 116, demographic data 118, lab test data 120, event data 122, SDI score data 124, pharmacy data 126, and patient data 128, may each be stored as structured data in any suitable type of data store.

The machine learning model data 114 may include any suitable data for training one or more machine learning models, such as historical claim data structures related to one or more of the claims data 116, demographic data 118, lab test data 120, event data 122, SDI score data 124, pharmacy data 126, and patient data 128. The machine learning model data 114 may include historical feature vector inputs that are used to train one or more machine learning models to generate a prediction output, such as a prediction of a mortality risk for patients within a specified future time period (for example, the next six months, the next year or the next two years).

In various implementations, users may run the machine learning model via the user device 106, to identify patients having a highest predicted mortality risk based on data specific to the patient, in order to schedule palliative care interventions or other case management for patients having the highest needs. The user device 106 may include any suitable user device for displaying text and receiving input from a user, including a desktop computer, a laptop computer, a tablet, a smartphone, etc. The user device 106 may access the database 102 directly, or may access the database 102 through one or more networks 104 and the system controller 108. Example networks may include a wireless network, a local area network (LAN), the Internet, a cellular network, etc.

The system controller 108 may include one or more modules for automated selection of executable sequences. For example, FIG. 1 illustrates a recommendation module 130, and a machine learning model training module 132. The recommendation module 130 may include one or more machine learning models, which may be trained by the machine learning model training module 132 based on the machine learning model data 114. The recommendation module 130 may use one or more of the claims data 116, demographic data 118, lab test data 120, event data 122, SDI score data 124, pharmacy data 126, and patient data 128, to generate an expiration prediction score for patients within a population of entries of the database 102.

As shown in FIG. 1, the system controller 108 may communicate with a palliative care intervention module 110 via the network(s) 104. For example, the output from the recommendation module 130 may be used to schedule palliative care interventions for high risk patients (such as those predicted to have the highest likelihood of dying within a specified future time period). Example interventions include, but are not limited to, sending text messages about suggested care, sending emails, automated phone calls, live physician or pharmacist phone calls, and scheduling the patient with a palliative care case management database.

Referring back to the database 102, the claims data 116 may include any suitable data related to medical claims of patients, such as ICD diagnosis codes like dementia, cancer, chronic respiratory disease, chronic kidney disease, heart failure, and stroke. The claims data 116 may include current procedure codes, a count of unique CPT codes, a count of unique diagnosis codes, a number of hospital stay days, a number of ICU admission days, a maximum CPT and diagnosis codes applied in a day, a cost of claims, and so on.

The demographic data 118 may include any suitable demographic data patient such as a patient's age, race, and sex. The lab test data 120 may include any suitable data regarding laboratory tests for patients, such as lab related CPT codes and a number of lab tests based on CPT codes. The event data 122 may include any suitable health events related to patients, such as a number of inpatient and outpatient hospitalizations and CT scan events.

The SDI score data 124 may include any suitable SDI information (which may be obtained based on the American community survey or other source), such as various localized measures of access to food, economic opportunities, infrastructure, levels of education, health coverage, cultural norms, and so on. These categories may be scored, ranked, or otherwise rated in various implementations. The pharmacy data 126 may include any suitable data related to pharmacy information, such as medicines like furosemide, an average number of medicines used by the patient per day, a number of unique medicines, a therapeutic area like antidepressants or antidiabetics, and so on. The patient data 128 may include any suitable data specific to patients, such as a last discharge disposition, wheelchair usage, and a number of days since a last inpatient or outpatient event. As mentioned above, in various implementations more or less (or other) data may be stored in the database 102.

Figure 2:
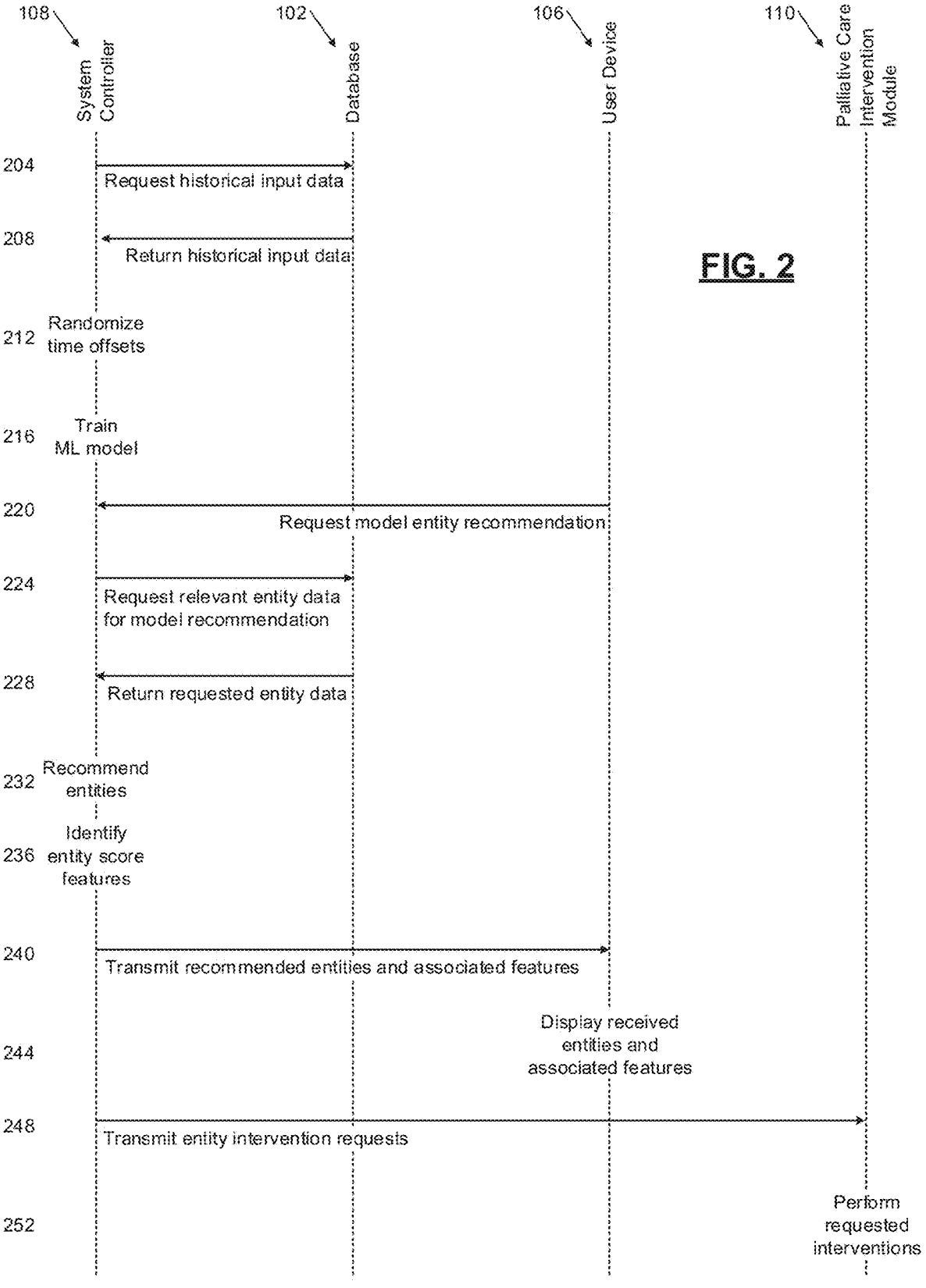
FIG. 2 is a message sequence chart illustrating example interactions between elements of the system of FIG. 1.

FIG. 2 is a message sequence chart illustrating example interactions between the system controller 108, the database 102, the user device 106, and the palliative care intervention module 110, during automated selection of executable sequences by the system 100. As shown in FIG. 2, the system controller 108 requests historical input data, such as the machine learning model data 114, at line 204. At line 208, the database 102 returns historical input data to the system controller 108.

At line 212, the system controller 108 randomizes time offsets for the historical input data, which may minimize seasonal or other time-related biases. For example, the machine learning model training module 132 may select a first patient from the historical input data, obtain an expiration date for the patient (such as a date that the patient died), and then generate a randomly selected offset value within a specified time window prior to the expiration date. The time window could be any suitable time period prior to the expiration date, such as a window of 6 to 12 my months prior to the expiration date, 0 to 12 months prior the expiration date, 1 to 2 years prior to the expiration date, and so on.

The randomization of the offset value may be achieved by iterating through a stored series of offset values. For example, this stored series may be generated at design time using a pseudorandom number generator. If the stored series is long enough, it can be repeated in a loop to achieve results insignificantly different from a truly random sequence. In other implementations, the offset value may be generated by a pseudorandom number generator on the fly. In various implementations, the pseudorandom number generator output may be, for example, uniformly distributed or normally distributed.

Once the random time offset is selected, the machine learning model training module 132 may obtain relevant patient data within a specified training time period prior to the randomly selected offset value. For example, if a random offset value is selected at nine months prior to the expiration date of the patient, the machine learning model training module 132 may obtain historical input data for the patient in the 12 months prior to the nine month offset value (such as data from 9 to 21 months before the expiration date). In various implementations, any suitable training time may be selected, such as six months, two years, and so on. Selecting a time period of at least one year may account for seasonal variations that could otherwise bias the training data, such as mortality rates changing during summer versus winter (for example, due to the flu), and other factors.

At line 216, the machine learning model training module 132 trains the machine learning model. The machine learning model may be trained using any suitable training techniques, such as example training techniques described further below with reference to FIG. 3. And as described further below, any suitable machine learning model may be used in various implementations.

The user device 106 requests a model entity recommendation at line 220. For example, the user may request to run the recommendation module 130 of the system controller 108 to identify patient entities in the database 102 having the highest risk of mortality within the future specified time period, such as the next six months, the next year, the next two years, and so on.

At line 224, the system controller 108 requests relevant entity data from the database 102 in order to perform the model entity recommendation. For example, the system controller 108, including the recommendation module 130, may request any of the claims data 116, demographic data 118, lab test data 120, event data 122, SDI score data 124, pharmacy data 126, and patient data 128, which is relevant to the patient entities associated with the model recommendation request. In various implementations, the recommendation request may be specified based on existing patients of a healthcare provider, existing patients of a specified health plan, healthcare patients in a geographic location, patients within a specified demographic group, and so on. At line 228, the database 102 returns the requested entity data to the recommendation module 130 of the system controller 108.

The recommendation module 130 of the system controller 108 recommends a specified number of entities, at line 232. For example, the recommendation module 130 may run the trained machine learning model to identify a specified number of patients having a highest mortality risk within a future specified time period, such as the next year.

At line 236, the recommendation module 130 of the system controller 108 identifies score features for each patient entity included in the recommendation output of the machine learning model. For example, the recommendation module 130 may determine which predictor variables had the largest impact on the recommendation score for a specific patient, such as input feature vector values for the patient that provided the greatest contribution to the recommendation score for the patient.

The system controller 108 then transmits the recommended entities and associated features to the user device 106, at line 240. The user device 106 displays the received entities and the associated features, at line 244. For example, a list of the highest mortality risk patients may be displayed on a screen of the user device 106 for a physician or administrator to determine palliative care recommendations for the patients.

At line 248, the system controller 108 transmits the intervention request to the palliative care intervention module 110. The palliative care intervention module 110 then performs requested interventions at line 252. For example, the palliative care intervention module 110 may send a text message to the patient, send an email to the patient, schedule an automated telephone call to the patient, or a arrange a live call from a physician or pharmacist. In various implementations, the palliative care intervention module 110 may schedule the patient entity to a case management database to perform palliative care actions for the patient.

Machine Learning Model

Figure 3:
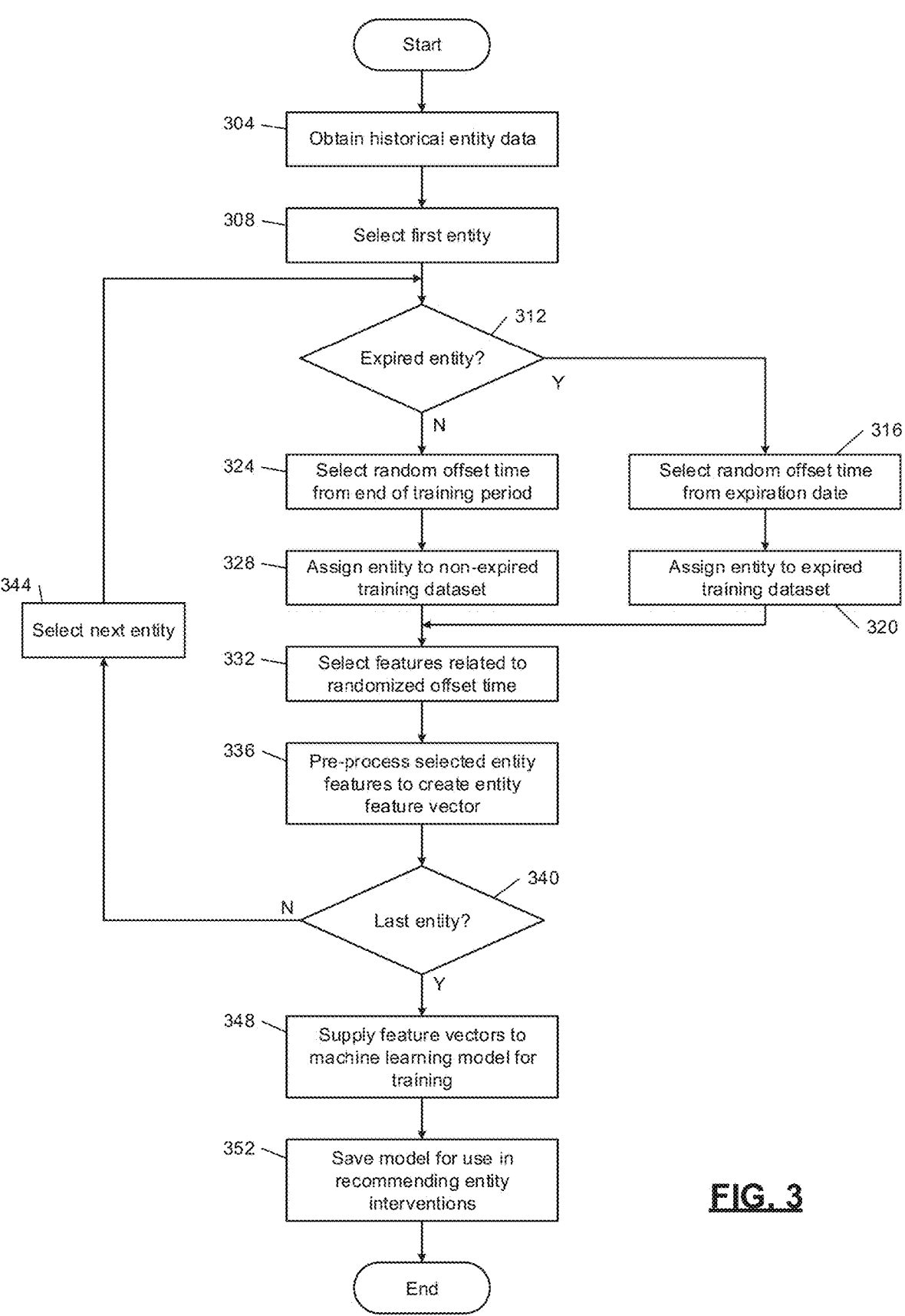
FIG. 3 is a flowchart illustrating an example process for training a machine learning model.

FIG. 3 illustrates an example process for generating a machine learning model (for example, using the machine learning model training module 132 of FIG. 1). At 304, control obtains historical entity data, such as from the database 102. The data may include any suitable data for developing the machine learning model. For example, the machine learning model data 114 from the database 102 may be used to generate historical feature vector inputs for training the machine learning model. The historical feature vector inputs may include, for example, one or more of claims data 116, demographic data 118, lab test data 120, event data 122, SDI score data 124, pharmacy data 126, and patient data 128, of the database 102 in FIG. 1.

At 308, control selects the first entity from the historical entity data. Control then determines whether the entity is an expired entity (such as a patient that has died), at 312. If so, control selects a random offset time from the expiration date, at 316. For example, and as described above, control may select any suitable offset time period prior to the expiration date of the patient, such as a randomly selected day within a window of 6 to 12 months prior to the expiration date. The random offset time may be selected on a daily basis within the specified time period, and historical data for the particular patient entity may be obtained within a training period prior to the random offset time. Control then assigns the entity to an expired training dataset, at 320.

If control determines at 312 that the selected entity is not an expired entity (such as a patient that is still alive), control proceeds to 324 to select a random offset time from the end of the training period. For example, control may identify an end date of the training data and then select a random offset time that is within the specified time window prior to the end date of the training data. The random offset time and specified time window for the non-expired training dataset may be the same as the expired training dataset, including the same randomization and distribution of offset times. Control then assigns the entity to the non-expired training dataset, at 328.

At 332, control selects features related to the random offset time value. For example, control may obtain historical input data parameters that correspond to the entity prior to the random offset time value, such as a medical history of the entity up to the random offset time value but not after. In various implementations, features may be selected from within a training window time period prior to the random offset time value, by including only appropriately dated information from one or more historical values of the claims data 116, demographic data 118, lab test data 120, event data 122, SDI score data 124, pharmacy data 126, and patient data 128.

At 336, control may pre-process selected entity features to create an input feature vector for the entity. For example, the input parameters may be formatted, standardized, bounded by minimum or maximum values, and so on, in order to create an input feature vector for supplying to train the model. In various implementations, feature engineering may be performed in order to determine the input feature vector format and parameters that provide the highest accuracy for the model, in order to improve model performance. The pre-processing may be performed using any suitable techniques, such as running a structured query language (SQL) script on an Arcadia database.

The feature engineering may be based on an analysis of specific input parameter values having the highest predicted value impact on the likelihood score generated by the model for each patient. For example, under demographic data, the age and gender parameters may have a highest impact on the likelihood output score for patients. Under medical claim features, example high importance features may include a number of unique CPT codes, an oxygen concentrator, an ICD code of unspecified dementia, chronic respiratory disease, a CPT code of subsequent nursing facility care, kidney disease, dementia, an ICD code for palliative care, a CPT code of hospice service, a cancer diagnosis, and a CPT code for an ambulance service.

Example lab related CPT values having a high impact on the prediction score may include, but are not limited to, a lipid panel, a strep assay, an influenza assay, a microscopic tissue exam, a general health panel, and a microbiology susceptible MIC. Example SDI score features having a high impact on the prediction output of the machine learning model may include an SDI infrastructure score, an unweighted average SDI score, an SDI food access score, and an SDI education score.

In other categories, pharmacy high importance features may include use of a furosemide medicine, a therapeutic group of antidepressants category, an average number of medicines per day, and an antidiabetic therapeutic group category. Example EMR features may include a count of electrocardiograms and sepsis occurrence. Encounter features having a high importance may include a number of service utilizations for both inpatient and outpatient care, and a CT scan count. Other high importance features may include, but are not limited to, a number of days since a last outpatient visit, use of a wheelchair, and a number of days since last inpatient visit.

Referring again to FIG. 3, control determines at 340 whether the last entity has been selected from the patient population of the historical input data. If not, control then selects a next entity at 344 and returns to 312 to determine if the next selected entity is an expired entity. Once control determines at 340 that the last entity in the historical input data has been processed, control proceeds to 348 to supply the feature vectors to the machine learning model for training. After training the model, control saves the model at 352 for use in recommending entity interventions. For example, multiple types of models may be tested, with the highest accuracy model being selected for use in entity recommendations.

In various implementations, control may separate the data obtained from the database 102 into training data and test data. The training data is used to train the model, and the test data is used to test model performance and prediction accuracy. Typically, the set of training data is selected to be larger than the set of test data, depending on the desired model development parameters. For example, the training data may include about seventy percent of the data acquired from the database 102, about eighty percent of the data, about ninety percent, and so on. The remaining thirty percent, twenty percent, or ten percent, is then used as the test data. When in training, the machine learning model may not capture information patterns or learn from the test data.

Separating a portion of the acquired data as test data allows for testing of the trained model against actual historical output data, to facilitate more accurate training and development of the model. This arrangement may allow the system controller 108 to simulate an outcome of the machine learning prediction when it processes a new patient entity in future scenarios. The model may be trained using any suitable machine learning model techniques, including those described herein, such as random forest, logistic regression, decision tree (for example, a light gradient boosted tree), and neural networks.

The trained model may be tested using the test data, and the results of the output data from the tested model may be compared to actual historical outputs of the test data, to determine a level of accuracy. The model results may be evaluated using any suitable machine learning model analysis, such as cumulative gain and lift charts. Lift is a measure of the effectiveness of a predictive model calculated as the ratio between the results obtained with and without the predictive model (for example, by comparing the tested model outputs to the actual outputs of the test data). Cumulative gains and lift charts provide visual aids for measuring model performance. Both charts include a lift curve and a baseline, where a greater area between the lift curve and the base line indicates a stronger model.

After evaluating the model test results, the model may be deployed if the model test results are satisfactory. Deploying the model may include using the model to make predictions for a large-scale input dataset with unknown outputs, and using the model to schedule interventions or other case management for high risk patients identified by the model. If the evaluation of the model test results is unsatisfactory, the model may be developed further using different parameters, using different modeling techniques, or using other model types.

Figure 4:
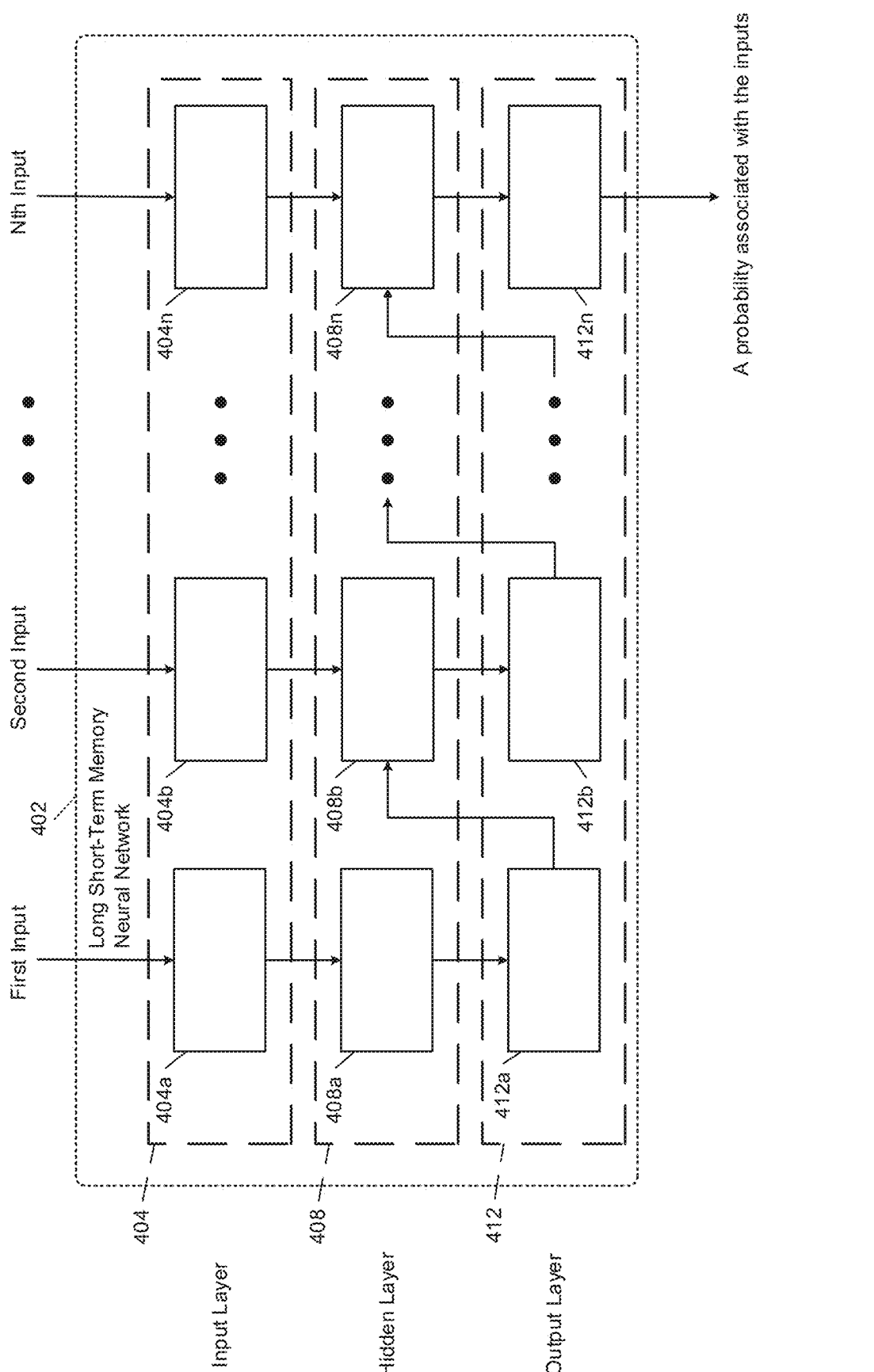
FIG. 4 is a graphical representation of layers or an example long short-term memory (LSTM) machine learning model.

FIG. 4 illustrates an example of a long short-term memory (LSTM) neural network used to generate models such as those described above with reference to FIG. 3, using machine learning techniques. Machine learning is a method used to devise complex models and algorithms that lend themselves to prediction (for example, future healthcare cost prediction). The models generated using machine learning, such as those described above with reference to FIG. 3, can produce reliable, repeatable decisions and results, and uncover hidden insights through learning from historical relationships and trends in the data.

The purpose of using the recurrent neural-network-based model, and training the model using machine learning as described above with reference to FIG. 3, may be to directly predict dependent variables without casting relationships between the variables into mathematical form. The neural network model includes a large number of virtual neurons operating in parallel and arranged in layers. The first layer is the input layer and receives raw input data. Each successive layer modifies outputs from a preceding layer and sends them to a next layer. The last layer is the output layer and produces output of the system.

FIG. 4 is a functional block diagram of a generic example LSTM neural network 402. The generic example LSTM neural network 402 may be used to implement the machine learning model trained by the process of FIG. 3, and various implementations may use other types of machine learning networks. The LSTM neural network 402 includes an input layer 404, a hidden layer 408, and an output layer 412. The input layer 404 includes inputs 404*a*, 404*b* . . . 404*n*. The hidden layer 408 includes neurons 408*a*, 408*b* . . . 408*n*. The output layer 412 includes outputs 412*a*, 412*b* . . . 412*n*.

Each neuron of the hidden layer 408 receives an input from the input layer 404 and outputs a value to the corresponding output in the output layer 412. For example, the neuron 408*a* receives an input from the input 404*a* and outputs a value to the output 412*a*. Each neuron, other than the neuron 408*a*, also receives an output of a previous neuron as an input. For example, the neuron 408*b* receives inputs from the input 404*b* and the output 412*a*. In this way the output of each neuron is fed forward to the next neuron in the hidden layer 408. The last output 412*n* in the output layer 412 outputs a probability associated with the inputs 404*a*-404*n*. Although the input layer 404, the hidden layer 408, and the output layer 412 are depicted as each including three elements, each layer may contain any number of elements.

In various implementations, each layer of the LSTM neural network 402 must include the same number of elements as each of the other layers of the LSTM neural network 402. For example, historical patient data may be processed to create the inputs 404*a*-404*n*. The output of the LSTM neural network 402 may represent a mortality risk of a patient within a future specified time period such as one year.

In some embodiments, a convolutional neural network may be implemented. Similar to LSTM neural networks, convolutional neural networks include an input layer, a hidden layer, and an output layer. However, in a convolutional neural network, the output layer includes one fewer output than the number of neurons in the hidden layer and each neuron is connected to each output. Additionally, each input in the input layer is connected to each neuron in the hidden layer. In other words, input 404*a* is connected to each of neurons 408*a*, 408*b*, . . . 408*n*.

In various implementations, each input node in the input layer may be associated with a numerical value, which can be any real number. In each layer, each connection that departs from an input node has a weight associated with it, which can also be any real number. In the input layer, the number of neurons equals number of features (columns) in a dataset. The output layer may have multiple continuous outputs.

As mentioned above, the layers between the input and output layers are hidden layers. The number of hidden layers can be one or more (one hidden layer may be sufficient for many applications). A neural network with no hidden layers can represent linear separable functions or decisions. A neural network with one hidden layer can perform continuous mapping from one finite space to another. A neural network with two hidden layers can approximate any smooth mapping to any accuracy.

The number of neurons can be optimized. At the beginning of training, a network configuration is more likely to have excess nodes. Some of the nodes may be removed from the network during training that would not noticeably affect network performance. For example, nodes with weights approaching zero after training can be removed (this process is called pruning). The number of neurons can cause underfitting (inability to adequately capture signals in dataset) or over-fitting (insufficient information to train all neurons; network performs well on training dataset but not on test dataset).

Various methods and criteria can be used to measure performance of a neural network model. For example, root mean squared error (RMSE) measures the average distance between observed values and model predictions. Coefficient of Determination ($R^2$) measures correlation (not accuracy) between observed and predicted outcomes. This method may not be reliable if the data has a large variance. Other performance measures include irreducible noise, model bias, and model variance. A high model bias for a model indicates that the model is not able to capture true relationship between predictors and the outcome. Model variance may indicate whether a model is not stable (a slight perturbation in the data will significantly change the model fit).

Automated Bias Correction Process

Figure 5:
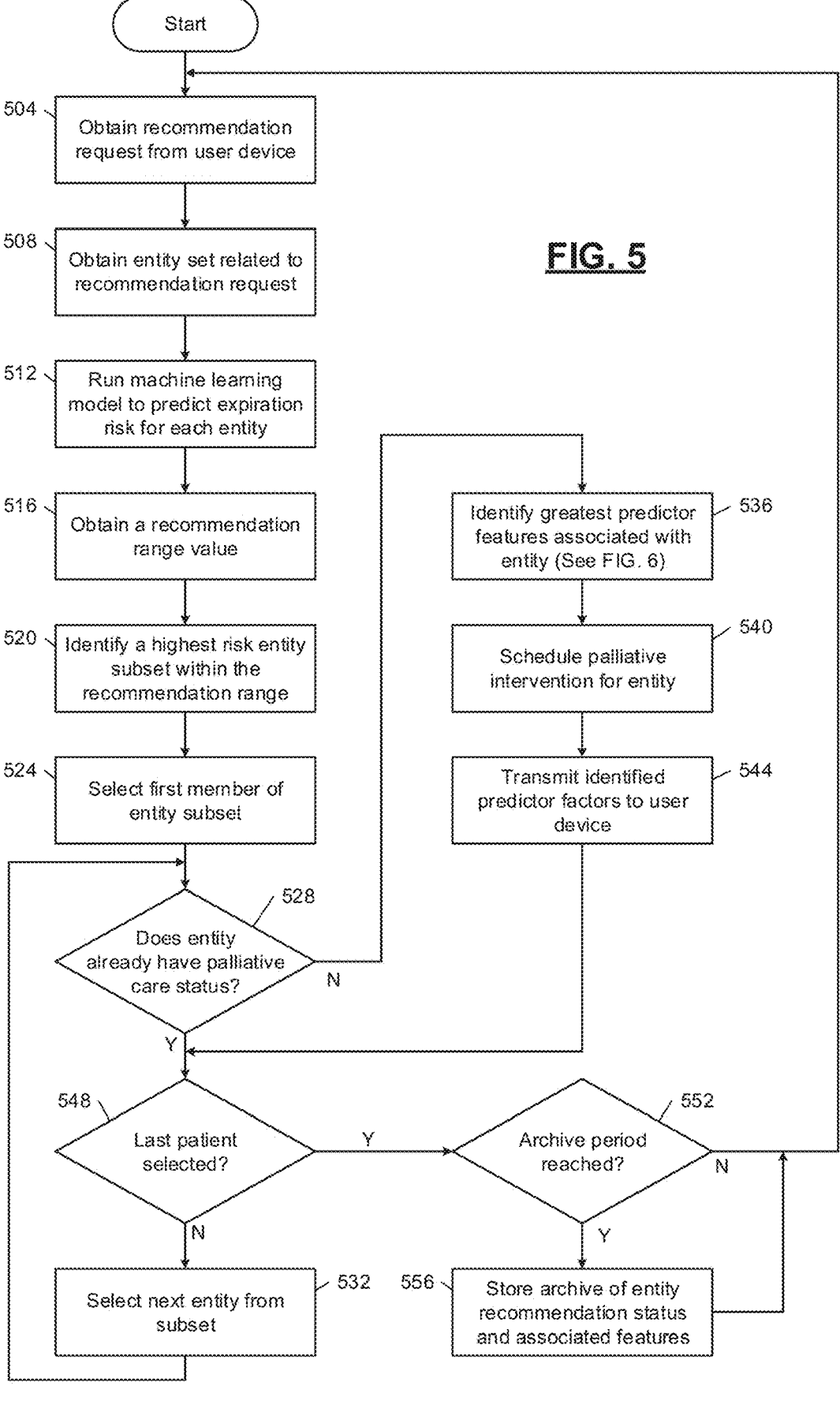
FIG. 5 is a flowchart illustrating an example process for automated selection of executable sequences.

FIG. 5 is a flowchart depicting an example process for automatically selecting an executable sequence. In various implementations, the example process may be performed by modules of the system controller 108, including the recommendation module 130. At 504, control begins by obtaining a recommendation request from the user device 106. For example, a user may request prediction of a likelihood of expiration within a specified future time period, for patients in a population.

At 508, control obtains an entity set related to the recommendation request. For example, control may obtain all patient entities from the database 102 that are related to a user request, such as patients belonging to a population specified by the user for generating mortality risk scores. In various implementations, a parameter table for the patients may be updated based on report generation options and a time period specified by a user for the inputs to the model. An SQL procedure may be run to prepare feature data for patients that are currently alive and belong to the target population.

Control runs the machine learning model at 512 to predict an expiration risk for each entity obtained at 508. For example, control may generate input feature vectors for each entity based on data from the database 102 that is specific to the entity, and submit the input feature vector to the trained machine learning model to generate a prediction score indicative of a likelihood the patient will die within a specified time period (such as the next year). In various implantations, a Python script may be run to call a DataRobot API to get mortality prediction scores and top ten features as part of a palliative care prediction report.

At 516, control obtains a recommendation range value. For example, a user may specify that they would like to identify the top 10% of patients in the population that have the highest mortality risk score. At 520, control identifies a subset of patients having the highest risk score that are within the recommendation range. For example, if the recommendation range is a top 10%, control may identify a top 10% of patients in the population having the highest risk output scores from the trained machine learning model.

Control proceeds to 524 to select the first member of the entity subset. At 528, control determines whether the entity already has palliative care status. For example, some patients in the database 102 may already be part of a palliative care program. If so, control may move onto the next patient because the current patient is already experiencing palliative care and no further action is needed from the recommendation module 130 for that specific patient. If control determines at 528 that the patient already has palliative care status, control proceeds to 548 to determine whether the last patient been selected. If not, control selects the next entity from the subset at 532, and then returns to 528 to determine whether the next selected entity has palliative care status.

If control determines at 528 that the entity does not have palliative care status, control proceeds to 536 to identify the greatest predictor features associated with the entity. Further examples of this process are discussed below with reference to FIG. 6. Briefly, identifying predictor features associated with an entity may include determining a specified number of input feature vector values having the largest impact on determining the mortality risk score for the patient. These input feature vector values may be compiled in a list associated with the patient and provided to a physician or administrator, in order to better determine palliative care eligibility for the patient.

At 540, control schedules a palliative care intervention for the entity. Scheduling of the palliative intervention may include, as described above, a live call from a physician or administrator, an automated phone call, sending an email, or sending a text message. An intervention may be considered as an executable sequence. For example, the intervention may be scheduled by control to be executed automatically by another system, the intervention may be executed by the physician or a family member of the patient, a list of recommended interventions may be transmitted to a provider along with the highest scoring patients, and so on. Control transmits identified predictor factors to the user device at 544.

After the last patient is selected at 548, control proceeds to 552 to determine whether an archive period has been reached. If so, control stores an archive of recommendation statuses and associated features for each patient, at 556. For example, the archive data may be stored in the historical recommendation data 134 of the archive 112 in FIG. 1. In various implementations, each month's palliative care report may be archived to a Teradata database for further analysis of patient score patterns. For example, a Python script may run to push a report to a Teradata database history table that stores reports for every month, and to push feature data to the Teradata database for future reference to historical feature values.

Figure 6:
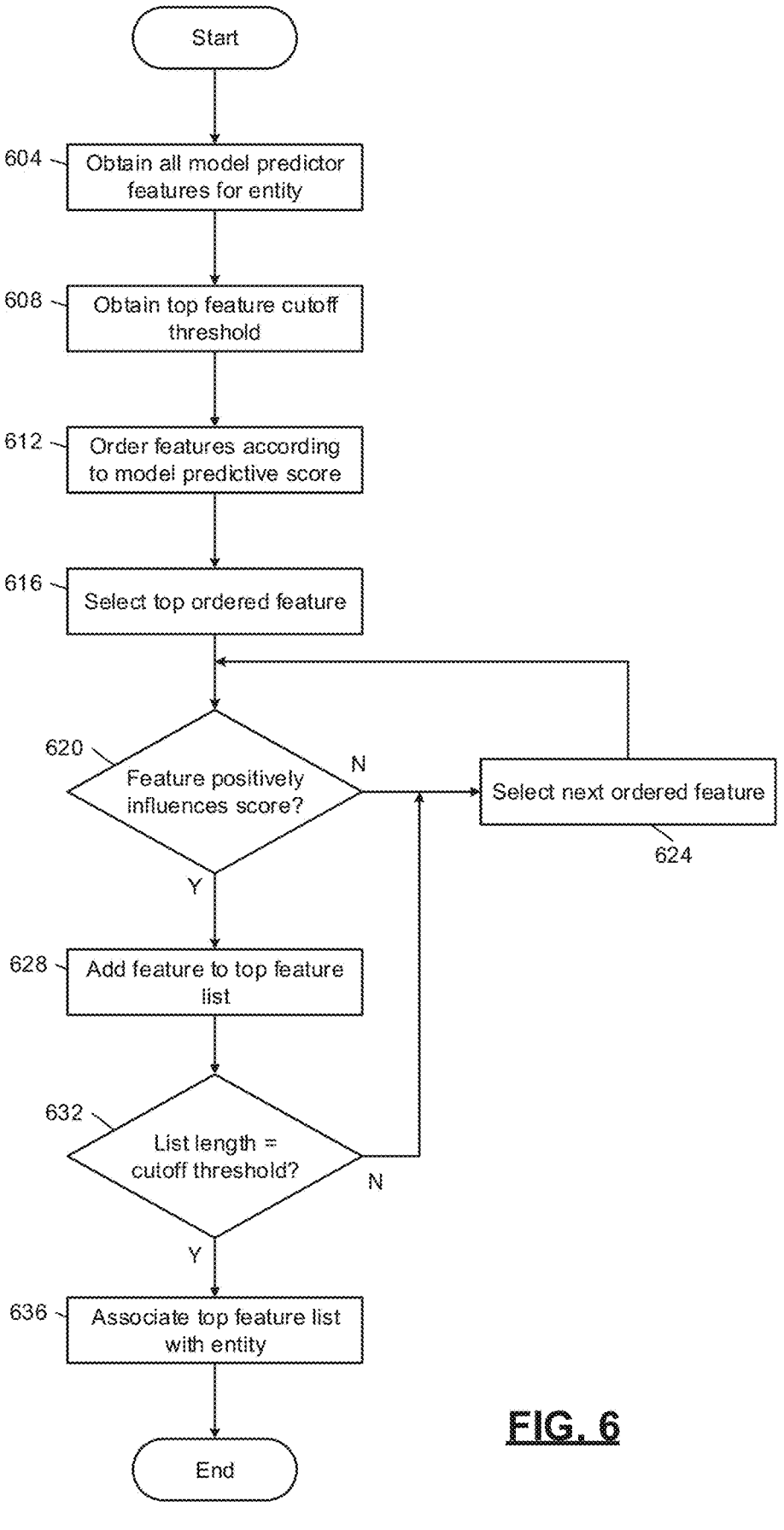
FIG. 6 is a flowchart illustrating an example process for generating an entity feature list.

FIG. 6 is a flowchart depicting an example process for generating a feature list for a database entity. At 604, control begins by obtaining all model predictor features for an entity. For example, control may obtain all values of an input vector that was created for the specific patient, as well as feature importance rankings generated by the recommendation module 130, for example, as the machine learning model process the data.

At 608, control obtains a top feature cutoff threshold. For example, a user may specify that they would like to receive a top 10 list of most impactful variables on the prediction score specific to a patient, in order to determine which factors played the largest role in predicting the future mortality risk for the patient. At 612, control orders the features according to the model predictive score impact for each feature. For example, control may determine which of all the input features has the highest impact on predicting the future mortality risk for a specific patient, and then store that determined input feature in a list associated with the patient. Control may then proceed to select the next highest input feature for the specific patient, and so on, until control obtains the top 10 features, or top 20 features, or whatever top feature cutoff threshold is specified by the user.

Control then proceeds to 616 to select the top ordered feature from the list. At 620, control determines whether the feature positively influences the prediction score (for example, whether the feature increased the likelihood prediction of the patient dying within the next year or other specified time period). If not, control selects the next ordered feature at 624, before returning to 620 to determine whether the next selected feature positively influences the score. This implementation may avoid confusing a physician or administrator, by leaving off input variables that contribute negatively to the score and suggest reasons that the patient should not have a high mortality risk.

If control determines the 620 that the feature positively influenced the score, control proceeds to 628 to add the feature to a top feature list associated with the patient entity. At 632, control determines whether the list length is equal to the cutoff threshold. If not, control returns to 624 to select a next ordered feature. Once the list length is equal to the cutoff threshold, such as the top 10 features that are most impactful on the prediction score for the patient, control proceeds to 636 to associate the top feature list with the patient entity.

FIG. 7 is a graphical representation of an example feature list for a database entry, such as a feature list generated by the example process of FIG. 6. The example feature list of FIG. 7 includes a prediction explanation for a hypothetical high risk patient, such as a patient having a high mortality risk score for a future specified time period of one year. In this example, the prediction score 0.8 may indicate a 0.8 likelihood prediction of the patient dying within the specified future time period.

The feature list of FIG. 7 includes 10 factors that have a highest impact on the prediction score for the patient. For example, factor one is the age of the patient, which has a value of 89 and had the largest impact on the prediction score of 0.8. Factor two is an international classification of diseases (ICD) code of 25, corresponding to an encounter for palliative care, and factor three is an ICD code of 1 corresponding to dementia.

Example factor four is a male gender of the patient, while factors five and six are current procedural terminology (CPT) codes of 99308 and A0428_BLS, indicating an ambulance service and emergency transport. Factor seven is a customer cost of a medical claim, having a value of $8,825. Factors eight and nine are medicines consumed by the patient including furosemide and ipratropium albuterol. Factor ten is a number of unique CPT codes applied to the patient, having a value of 28 in this example.

As explained above, these 10 factors may represent the specific input parameter values that have a greatest impact on the predicted score for this patient. The example feature list may provide the physician or administrator with further insights into specific reasons behind the predicted score for patient, in order to better target interventions or further assist the physician administrator in determining whether to suggest palliative care for the patient.

The feature list may be provided so that the individual prediction scores are accompanied with actionable interpretations for each patient. For example, model users may be able to rely on the recommendation model as providing accurate prediction assessments that are unbiased and consistent, based on the features included in the list for verification. The feature list may be generated using any suitable techniques, including an eXemplar based explanation of model predictions (XEMP) framework for interpretability.

In various implementations, machine learning models may be used to predict mortality likelihood scores for patient entities of a population, within a specified future time period such as one year. The models may empower providers with access to prescriptive palliative care opportunities without requiring manual review of patient records, and may allow for use of historical data for proactive insights into patient care. Insights may be provided for each patient, including key predictor features from the mortality score assigned to the patient. Post interventions may be expected to improve customer quality-of-life, as well as realize cost savings to providers and insurers by avoiding extraneous emergency room and patient costs.

In various implementations, a patient score in the top decile of a model output may have approximately a five times greater risk of mortality within the next 3 to 12 months as compared to a randomly selected patients (and nine times or more risk of mortality compared to manually selected patients). A patient in the top 5% of the model risk stratification may have a predicted mortality accuracy of 27% within the first year, and 51% in the next one to three years. Using the model to schedule palliative care interventions for case management may reduce insurer or provider costs by thousands to tens of thousands, or even more, for each patient recommended by the model.

CONCLUSION

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. In the written description and claims, one or more steps within a method may be executed in a different order (or concurrently) without altering the principles of the present disclosure. Similarly, one or more instructions stored in a non-transitory computer-readable medium may be executed in different order (or concurrently) without altering the principles of the present disclosure. Unless indicated otherwise, numbering or other labeling of instructions or method steps is done for convenient reference, not to indicate a fixed order.

Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements.

The phrase "at least one of A, B, and C" should be construed to mean a logical (A OR B OR C), using a non-exclusive logical OR, and should not be construed to mean "at least one of A, at least one of B, and at least one of C." The term "set" does not necessarily exclude the empty set. The term "non-empty set" may be used to indicate exclusion of the empty set. The term "subset" does not necessarily require a proper subset. In other words, a first subset of a first set may be coextensive with (equal to) the first set.

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are IEEE Standard 802.15.4 (including the ZIGBEE standard from the ZigBee Alliance) and, from the Bluetooth Special Interest Group (SIG), the BLUETOOTH wireless networking standard (including Core Specification versions 3.0, 4.0, 4.1, 4.2, 5.0, and 5.1 from the Bluetooth SIG).

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module. For example, the client module may include a native or web application executing on a client device and in network communication with the server module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. Such apparatuses and methods may be described as computerized apparatuses and computerized methods. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A computer system comprising:

memory hardware configured to store a machine learning model for automated bias correction, historical feature vector inputs, and computer-executable instructions for an artificial neural network, wherein the historical feature vector inputs include historical data structures specific to multiple historical database entities; and artificial neural network processor hardware configured to execute the instructions on a plurality of weighted nodes, wherein the instructions include:

training the machine learning model with the historical feature vector inputs to the artificial neural network to generate an entity expiration likelihood output, wherein the training includes, for each expired entity of the multiple historical database entities:

determining an expiration date of the expired entity; and minimizing seasonal bias in the historical data structures by generating a random offset time value for the expired entity, wherein generating the random offset time value includes randomly selecting a day within a time period prior to the expiration date of the historical database entity, and wherein the historical feature vector input for the expired entity includes only historical data structures that are dated prior to the expiration date of the expired entity minus the random offset time value;

obtaining a set of multiple database entities;

for each database entity in the set of multiple database entities:

obtaining structured input data specific to the database entity;

generating a feature vector input according to the structured input data;

processing, by the machine learning model, the feature vector input to generate the entity expiration likelihood output from the artificial neural network; and storing the entity expiration likelihood output in association with the database entity;

determining a subset of the multiple database entities having the highest entity expiration likelihood outputs; and for each database entity in the subset:

determining output impact scores for parameters of the feature vector input associated with the database entity, each output impact score indicative of an effect of the parameter on the entity expiration likelihood output for the database entity;

generating a feature list based on the determined output impact scores, wherein the feature list is specific to the database entity and includes one or more of the parameters having the highest output impact scores; and automatically selecting an executable sequence according to the entity expiration likelihood output associated with the database entity to perform automated bias correction.

2. The system of claim 1 wherein:

training the machine learning model includes generating a random offset time value for each non-expired entity of the multiple historical database entities;

the historical feature vector input for each non-expired entity includes only historical data structures that are dated prior to an end date of the historical data structures specific to the non-expired entity minus the random offset time value; and a distribution of the random offset time values for the expired entities is equal to a distribution of the random offset time values for the non-expired entities.

3. The system of claim 1 wherein generating the feature list includes, for each of the one or more parameters, removing the parameter from the feature list in response to determining that the parameter is negatively correlated with the entity expiration likelihood output for the database entity.

4. The system of claim 1 wherein the instructions further include:

generating an archive report including the entity expiration likelihood output and feature list for each database entity in the subset; and storing the archive report in an archive database on a periodic basis.

5. The system of claim 1 wherein automatically selecting the executable sequence includes automatically scheduling a palliative care intervention for the database entity.

6. The system of claim 5 wherein the palliative care intervention includes at least one of a text message intervention, an email intervention, an automated phone call intervention, and a live phone call intervention.

7. The system of claim 1 wherein automatically selecting the executable sequence includes automatically scheduling the database entity to a palliative care case management database.

8. The system of claim 1 wherein training the machine learning model includes:

comparing multiple entity expiration likelihood outputs of the machine learning model to the historical data structures;

determining whether an accuracy of the comparison is greater than or equal to a specified accuracy threshold;

adjusting parameters of the machine learning model or selecting a different machine learning model type for retraining the machine learning model, in response to the accuracy of the comparison being less than the specified accuracy threshold; and saving the machine learning model for use in generating entity expiration likelihood outputs, in response to the accuracy of the comparison being greater than or equal to the specified accuracy threshold.

9. The computer system of claim 1 wherein training the machine learning model includes:

training multiple machine learning model types simultaneously or in succession;

identifying one of the multiple machine learning model types having a highest output accuracy compared to others of the machine learning model types; and saving the identified machine learning model type having the highest output accuracy for use in generating entity expiration likelihood outputs.

10. The system of claim 1 wherein training the machine learning model includes:

separating portions of the historical feature vector inputs into structured training data and structured test data;

training the machine learning model using the structured training data;

testing the trained machine learning model using the structured test data;

evaluating results of testing the trained machine learning model; and saving the machine learning model for use in generating entity expiration likelihood outputs, in response to an accuracy of the evaluated results being greater than or equal to a specified accuracy threshold.

11. The system of claim 1 wherein training the machine learning model includes training a light gradient boosted tree model.

12. The system of claim 1 wherein generating the feature vector input includes generating the feature vector input according to at least one of structured claim data specific to the database entity, structured demographic data specific to the database entity, structured lab test data specific to the database entity, structured event data specific to the database entity, structured social depravation index (SDI) score data specific to the database entity, structured pharmacy data specific to the database entity, and structured patient data specific to the database entity.

13. The system of claim 1 wherein:

the time period is a six to twelve month time period prior to the expiration date of the historical database entity; and the historical feature vector input for the expired entity includes only historical data structures that are dated within a twelve month time period prior to the expiration date of the expired entity minus the random offset time value.

14. A computerized method for automated selection of executable sequences, the method comprising:

training a machine learning model with an artificial neural network and historical feature vector inputs to generate an entity expiration likelihood output for automated bias correction, wherein the historical feature vector inputs include historical data structures specific to multiple historical database entities, and wherein the training uses weighted nodes in the artificial neural network and includes, for each expired entity of the multiple historical database entities:

determining an expiration date of the expired entity; and minimizing seasonal bias in the historical data structures by generating a random offset time value for the expired entity, wherein generating the random offset time value includes randomly selecting a day within a time period prior to the expiration date of the historical database entity, and wherein the historical feature vector input for the expired entity includes only historical data structures that are dated prior to the expiration date of the expired entity minus the random offset time value;

obtaining a set of multiple database entities;

for each database entity in the set of multiple database entities:

obtaining structured input data specific to the database entity;

generating a feature vector input according to the structured input data;

processing, by the machine learning model, the feature vector input to generate the entity expiration likelihood output; and storing the entity expiration likelihood output in association with the database entity;

determining a subset of the multiple database entities having the highest entity expiration likelihood outputs; and for each database entity in the subset:

determining output impact scores for parameters of the feature vector input associated with the database entity, each output impact score indicative of an effect of the parameter on the entity expiration likelihood output for the database entity;

generating a feature list based on the determined output impact scores, wherein the feature list is specific to the database entity and includes one or more of the parameters having the highest output impact scores; and automatically selecting an executable sequence according to the entity expiration likelihood output associated with the database entity.

15. The method of claim 14 wherein:

training the machine learning model includes generating a random offset time value for each non-expired entity of the multiple historical database entities;

the historical feature vector input for each non-expired entity includes only historical data structures that are dated prior to an end date of the historical data structures specific to the non-expired entity minus the random offset time value; and a distribution of the random offset time values for the expired entities is equal to a distribution of the random offset time values for the non-expired entities.

16. The method of claim 14 wherein generating the feature list includes, for each of the one or more parameters, removing the parameter from the feature list in response to determining that the parameter is negatively correlated with the entity expiration likelihood output for the database entity.

17. The method of claim 14 further comprising:

generating an archive report including the entity expiration likelihood output and feature list for each database entity in the subset; and storing the archive report in an archive database on a periodic basis.

18. The method of claim 14 wherein automatically selecting the executable sequence includes automatically scheduling a palliative care intervention for the database entity.

19. The method of claim 18 wherein the palliative care intervention includes at least one of a text message intervention, an email intervention, an automated phone call intervention, and a live phone call intervention.

20. The method of claim 14 wherein automatically selecting the executable sequence includes automatically scheduling the database entity to a palliative care case management database.

* * * * *